United States Patent [19]

Sibalis

[11] Patent Number: 4,808,152
[45] Date of Patent: Feb. 28, 1989

[54] SYSTEM AND METHOD FOR CONTROLLING RATE OF ELECTROKINETIC DELIVERY OF A DRUG

[75] Inventor: Dan Sibalis, Stony Brook, N.Y.

[73] Assignee: Drug Delivery Systems Inc., New York, N.Y.

[21] Appl. No.: 554

[22] Filed: Jan. 5, 1987

Related U.S. Application Data

[63] Continuation-in-part of Ser. No. 524,252, Aug. 18, 1983, Pat. No. 4,557,723, and a continuation-in-part of Ser. No. 660,192, Oct. 12, 1984, Pat. No. 4,622,031, and a continuation-in-part of Ser. No. 702,486, Feb. 19, 1985, abandoned, and a continuation of PCT US85/01074, filed Jun. 10, 1985, published as WO86/07268 on Dec. 18, 1986.

[51] Int. Cl.$^4$ .............................................. A61F 2/38
[52] U.S. Cl. ...................................... 604/20; 128/798; 29/825
[58] Field of Search ............... 128/783, 798, 799, 802, 128/803; 604/20; 29/825, 874, 876, 877, 878

[56] References Cited

U.S. PATENT DOCUMENTS 4,406,658 9/1983 Lattin et al. .................... 604/20
4,474,570 10/1984 Arivra et al. .................... 604/20

FOREIGN PATENT DOCUMENTS 2263792 10/1975 France ............................. 604/20

*Primary Examiner*—Edward M. Coven
*Assistant Examiner*—Randy Citrin
*Attorney, Agent, or Firm*—Lackenbach Siegel Marzullo & Aronson

[57] ABSTRACT

This invention relates to a system and method for controlling the rate of electrokinetic delivery of a drug or drugs through the skin (42) or mucous membrane of a human or animal being by way of a drug reservoir (12) having a pair of electrodes (16,18) positioned in the reservoir (12) that are connected to first (22A) and second (22B) power sources. The first (22A) and second (22B) power sources can be optionally directed to the electrodes (16, 18) to add to or subtract from the second (22B) power source so as to cause variations in the drug reservoir (12) in accordance with the type of drug being administered. The system can include computer (62) directed controls (66) programmed for the particular drug. With such pre-programmed variations in the drug reservoir (12), control of the rate of drug delivery through the skin (42) can be regulated or pre-set by prescription.

22 Claims, 2 Drawing Sheets

SYSTEM AND METHOD FOR CONTROLLING RATE OF ELECTROKINETIC DELIVERY OF A DRUG

This application is a continuation of applicant's International Patent Application PCT/US85/01074; filed June 10, 1985.

RELATED U.S. PATENT APPLICATIONS

The invention disclosed and claimed in this patent application is a continuation-in-part of my earlier filed U.S. patent applications, Ser. No. 524,252, filed Aug. 18, 1983 (now U.S. Pat. No. 4,557,723); and Ser. No. 660,192, filed Oct. 12, 1984 (now U.S. Pat. No. 4,622,031); and Ser. No. 702,486, filed Feb. 19, 1983 (abandoned), and is also a continuation of PCT/US85/01074, filed June 10, 1985, published as WO86/07268 on Dec. 18, 1986, all of which priority is hereby based upon and claimed under 35 U.S.C. 120 for all these earlier filed patent applications.

BACKGROUND OF THE INVENTION

It is known that the skin is permeable to certain compounds, such as nitroglycerine and scopolamine; or the skin could be made more permeable by other means, such as by the use of solvents, or other types of enhancers, such as physical means or chemical enhancers. Thus, presently the rate of drug delivery is controlled by a semi-permeable membrane, for example, in an osmotic profusion type drug applicator. Such drug applicators are currently marketed and in use for the transdermal delivery of nitroglycerine and scopolamine. These systems, however, are limited just to drugs which are soluble in both water and oil, are of low molecular weight, and are potent in small concentrations. Consequently, there are very few drugs which can be utilized with this modality of delivery. In addition, it is very difficult to consistently produce a membrane or a matrix which ensures a predictable rate of drug delivery.

The delivery of a drug from a drug reservoir can be accomplished by electrokinetic effect, that is, either by iontophoresis, electrophoresis or by electro-osmosis. Further, the rate of delivery is affected by the amount of electric current applied between the skin and the drug reservoir. Further, the electric current affects both the skin of the patient and the drug reservoir independently so as to create conditions that increase or decrease the rate of delivery of the drug through the skin of the patient. For example, current will affect the pH of the skin at the interface between the membrane of the reservoir, or patch area. Also, a polarization of the skin will change skin permeability. The charge of the drug particles, or ionic charge, will cause repulsed direction of the ionized drug through the skin. Also, an electro-osmotic effect is created at the skin surface or mucous membrane by electric current. As for the drug reservoir of the patch, electrical current passed through the drug, which is contained in the drug reservoir, can control or improve mobility of the drug thus allowing less current to be needed for drug movement into the skin or mucous membrane. Also, the natural diffusion of the drug compound acts within the patch and is controlled in either additive or subtractive fashion by sending an electric current through the drug independently of the current through the skin; the rate of delivery and the degree of concentration of the drug at the skin can be affected and independently controlled. Also, the pH of the drug within the patch near the skin can thus be changed by electric current. Also, electric current in the patch can cause electrolysis, thus activating in sequence pre-existing buffering agents in the drug reservoir. In summary, control of the rate of delivery of a drug from a drug reservoir through the skin can be controlled by independent but simultaneous currents through the patch and through the skin. It is hereby noted that descriptions relating to mass transfer activity by application of electric current is contained in the applicant's earlier filed U.S. patent applications, Ser. Nos. 524,252, 660,192, PCT/US/85/00080, 702,486, and my application Ser. No. 000,555, filed Jan. 5, 1987, entitled "Programmable Control and Mounting System for Transdermal Drug Applicator", filed concurrently herewith as co-inventor. All of the disclosures contained in these earlier filed U.S. patent applications are hereby expressly incorporated herein by reference.

It is therefore an object of the present invention to control the rate of delivery of a drug from a drug reservoir by placing a plurality of electrodes within the reservoir in electrical circuit means with first and second power sources and with the skin or mucous membrane, the patch of the first power source being optionally directed to one of the two electrodes so as to cause the second power source to be added or subtracted from the first power source for current directed through the skin.

SUMMARY OF THE INVENTION

In order to achieve the objectives listed above and other objects that will become evident in the detailed description of the invention which follows, a system is provided for selectively controlling the rate of delivery of a medicament or drug through the skin or mucous membrane of a human or animal patient by electrokinetic action. The system includes, in combination, drug reservoir means containing a first drug, with the drug reservoir means in contact with the skin of the patient, and being for storing the drug and being capable of passing an electrical current through the drug wherein the drug is passed into the skin of the patient by electrokinetic action at a first skin contact. A pair of spaced first and second electrodes is positioned in the drug reservoir means; and electrode means in electrical contact with the skin of the patient at a second skin contact spaced from the first skin contact passes and receives current to and from the second skin contact. A first electrical circuit extends between the first and second electrodes, between the second electrode and the first skin contact, through the skin of the patient between the first and second skin contacts, between the second skin contact and the electrode means, and between the said electrode means and the first electrode. The second electrical circuit includes circuit path means with the first electrical circuit, the second electrical circuit extending between the first and second electrodes, the second electrode and through the circuit means, and to the first electrode, the first electrical circuit, including a bypass circuit path extending between a junction positioned on the first electrical circuit and the second electrode, the junction being positioned between the electrode means and the first electrode. First power means is positioned in the first electrical circuit between the electrode means and the junction, the first power means is for generating a first electrical current through the first circuit. A second power means is positioned in the second electrical circuit on the electrical path means for passing a second electrical current through the second circuit; and means for passing a selected current between the first and second electrodes in accordance with the dosage and type of drug in the reservoir means. Such means for passing a selected current includes a plurality of selected options:

(a) selectively passing only the first current in the first circuit;

(b) selectively passing only the second current in the second circuit;

(d) selectively inactivating the bypass circuit;

(d) selectively using only the bypass circuit;

(e) selectively positioning the polarity of the first power means; and (f) selectively positioning the polarity of the second power means;

whereby a predetermined rate of electrokinetic delivery of the drug is attained.

Also included in the present invention is a control system adapted to selectively operate the means for passing a selected current; and a switch positioned at the junction on the first circuit is adapted to selectively activate or deactivate the bypass circuit and simultaneously to deactivate or activate, respectively, the first circuit between the junction and the first electrode. The control system includes a computer system positioned proximate the first and second circuits, the computer system including signal circuits connected to the means for passing a selected current, computer originated output controls aligned with the signal circuits, and computer programming input circuitry capable of instructing the computer relative to operating the output controls. Also, another reservoir means includes a semipermeable membrane capable of passing the second drug extending across the reservoir forming third and fourth reservoirs generally lateral to the skin of the patient. The third and fourth reservoirs are distal and proximate respectively to the skin of the patient, and the second drug is in generally concentrated form in the third reservoir and in generally diluted form in the fourth reservoir.

Also a method of manufacturing the system described above is set forth in the detailed description that follows.

It is another object of the present invention to control the rate of delivery of a drug from a drug reservoir by controlling current flow within the drug reservoir and/or at the skin surface or mucous membrane so as to cause physical and chemical changes of the drug environment within the reservoir and/or at the skin or mucous membrane that are related to the rate of flow of the drug from the reservoir through the skin.

It is another object of the present invention to control the rate of delivery of a drug from a drug reservoir by controlling current flow within the drug reservoir and/or at the skin so as to cause physical and chemical changes of the drug within the reservoir and at the skin that are related to the rate of flow of the drug from the reservoir through the skin.

BRIEF DESCRIPTION OF THE DRAWINGS

The aforementioned aspects and other features of the invention are explained in the following description taken in connection with the accompanying drawings wherein.

DESCRIPTION OF THE PREFERRED EMBODIMENTS

Reference is now made to the drawings in which the same or similar elements are referred to throughout the disclosure by the same numerals.

Figure 1:
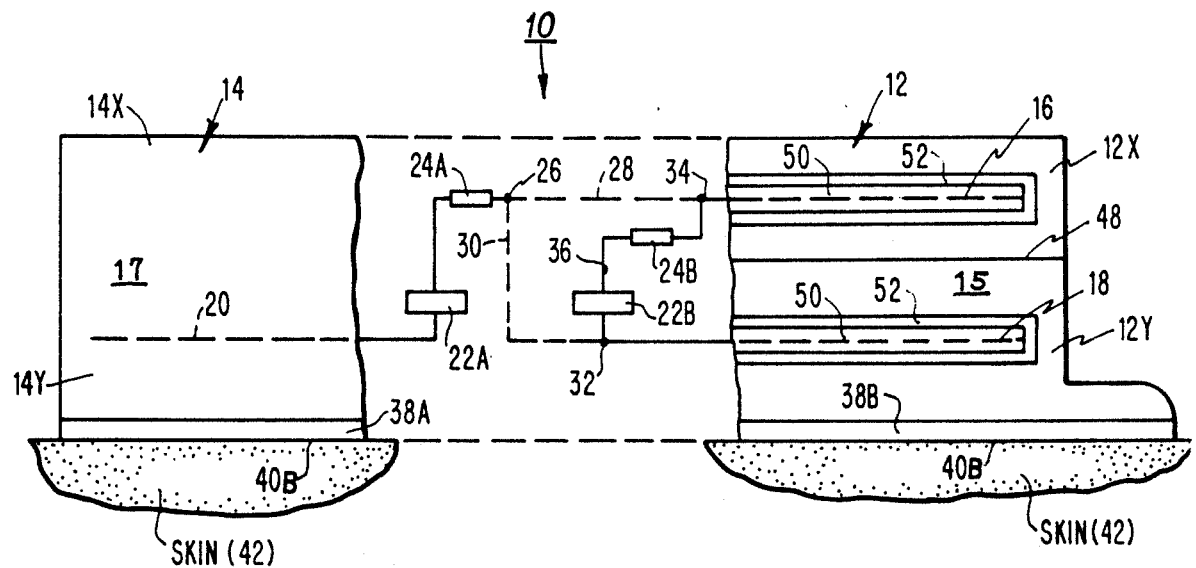
FIG. 1 is a schematic diagram illustrating the electrode configurations applicable for controlling the rate of delivery of drug medicaments transdermally.
Figure 2:
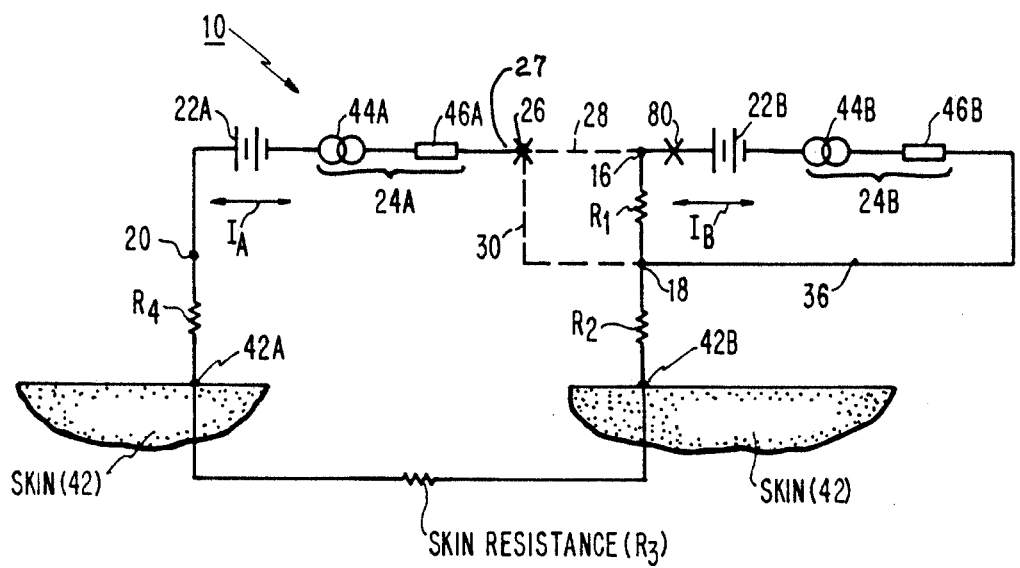
FIG. 2 is an electrical diagram equivalent to the schematic shown in FIG. 1.

A drug applicator system 10 shown in FIGS. 1 and 2 includes a pair of drug reservoirs 12 and 14.

Each drug reservoir 12 and 14 preferably contains a different drug preferably contained in a gel, such as a water-soluble gel, or a suitable matrix. The gel-drug mixtures are indicated as 15 and 17 in reservoirs 12 and 14 respectively. Each drug reservoir 12 and 14 includes top and side walls impermeable to the passage of drugs 15 and 17 and a bottom wall permeable to the passage of drugs 15 and 17.

A pair of spaced generally parallel electrodes shown here as upper electrode 16 and lower electrode 18 are positioned in reservoir 12 and a single (third) electrode 20 is positioned in reservoir 14. A first power source, such as a battery 22A, is positioned in series with electrode 20 and electrodes 12 or 18. A first current conditioning means 24A is positioned between battery 22A and electrodes 16 and 18.

A first circuit, represented by and through which a current $I_A$ flows is shown to electrically connect the skin in series with the two electrodes 16 and 18 and the third electrode 20. A by-pass electrical circuit path 30, connects the first circuit directly with lower electrode 18 by-passing upper electrode 16. The by-pass circuit extends from a junction 26 in the first circuit. An electrical path 28 extends from junction 26 to upper electrode 16 to complete the first circuit. A switch 27 is placed at junction 26 for the purpose of electrically controlling the paths 28 or 30, which as can be seen hereinafter provide the additive or subtractive nature of the current control.

Figure 3:
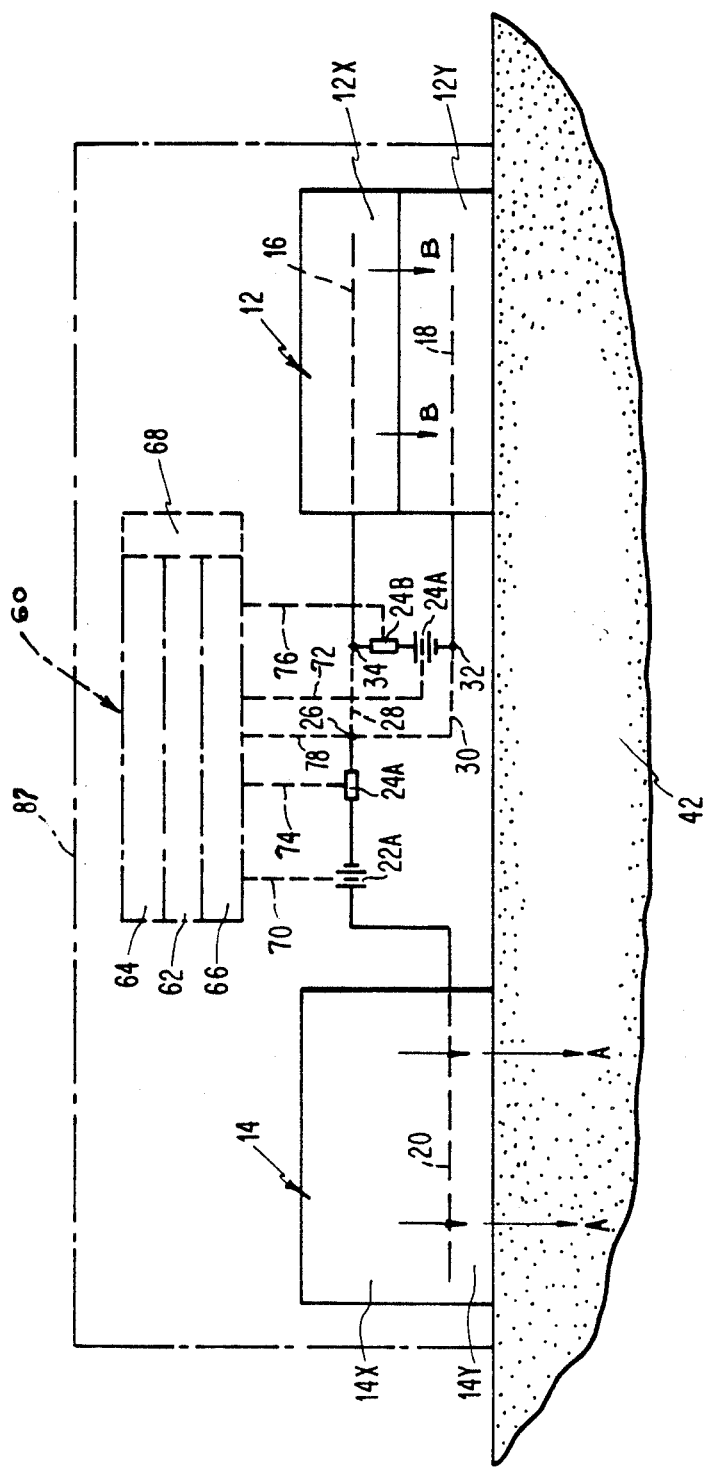
FIG. 3 is a schematic diagram illustrating the movement of the drugs from the drug reservoirs and schematically illustrating a computer control mechanism in phantom lines.

A second electrical path 36 is shown in parallel with electrodes 16 and 18. An electrical current $I_B$ passes through electrical path 36. Second electrical path 36 is shown in FIG. 1 as extending between upper junction 34 and lower junction 32 or by-pass electrical paths 28 and 30, respectively. An electrical path 36 connects junctions 32 and 34. A second power source, such as second battery 22B is in series with a second current conditioning means 24B on path 36 with the conditioning means 24B being positioned on electrical path 36. Electrically conductive membranes 38A and 38B are each capable of passing a particular drug from the bottom walls of reservoirs 14 and 12 respectively. Electrically conductive skin adhesives 40A and 40B extend along the bottom surfaces of membranes 38A and 38B respectively; adhesives 40A and 40B are in adhesive contact with the skin 42 of the patent, shown as skin or mucous membrane 42A at the electrical contact at the reservoir 14 and as skin or mucous membrane 42B at the electrical contact at reservoir 12, respectively. FIG. 2 illustrates resistances in the system as follows: $R_1$ between electrodes 16 and 18, shown in FIG. 2 schematically as junctions 16 and 18; $R_2$ between electrode 18 and skin contact 42B; $R_3$ for the skin resistance between skin contacts 42A and 42B; and $R_4$ between skin contact, 42A and electrode 20. Current conditioning means 24A is set forth in FIG. 2 as a constant current diode 44A and timer 46A in series; and the current conditioning means 24B is set forth also as a constant current diode 44B and timer 46B in series. First battery 22A generates current $I_A$ and second battery 22B generates current $I_B$. As indicated in FIG. 3, currents $I_A$ and $I_B$ are reversible in accordance with the capability of first and second batteries 22A and 22B to reverse their polarities upon command independently of one another. In addition, electrical paths 28 and 30 are either/or paths that are selectable upon predetermined command, preferably by activation of a switch 27 at junction 26 or are connected or not connected upon the circuit board or its equivalent during the manufacturing process in accordance with the drug being used and the current desired with the selected drug for prescribing a desired dosage within a particular time frame.

When batteries 22A and 22B are operating in a mode of operation wherein a current passes from reservoir 12 through resistance $R_2$ to skin contact 42B, the current will be carried through skin 42, or mucous membrane schematically shown as skin resistance $R_3$, to skin or mucous membrane contact 42A, through $R_3$ to electrode 20 and then to first battery 22A. When the polarity of battery 22A is reversed wherein the electrode 20 side is positive, the current described above will be completely reversed.

The above circuit provides a number of selected current options for the patient or the prescriber of the medication. These options will be set forth below. It is to be particularly noted that because of the spaced electrodes 16 and 18 in reservoir 12 and the circuits and polarities that can be selected relative to electrodes 16 and 18, a particular drug contained in reservoir 12 can be conditioned in accordance with the current options. The current options are as follows:

(a) $I_A = 0$. In this option, no current passes through skin contact 42B at reservoir 12. $I_B$ moves in a continuous circuit in one direction or another between electrodes 16 and 18 and path 36. In this option, the current $I_B$ is used only for the purpose of using the current to change the chemistry of the drug in reservoir 12. The quantity of current $I_B$ is determined by current conducting means 24B.

(b) Circuit 30 is selected and circuit 28 is left open by operation of a switch 27 at junction 26. Option currents $I_A$ and $I_B$ each follow independent paths, with $I_A$ travelling to skin or mucous membrane contact point 42B and $I_B$ moving in its own circuit on path 36 between electrodes 16 and 18 so as to treat the drug in reservoir 12 which $I_A$ acts to move the drug into skin or mucous membrane 42. It is to be noted that $I_A$ and $I_B$ may each be reversed by reversing the polarity of first and second batteries 22A and 22B independently of one another. There are four different sub-options of current configurations in this option.

(c) Circuit 28 is selected and circuit 30 is left open. This option results in $\pm I_A \pm I_B$ depending on which polarity is selected for batteries 22A and 22B.

(d) Circuit 28 is selected, circuit 30 is left open and $I_B = 0$. This is the most elementary of the options since $I_A$ will be used simply to move the charged drug by electrokinetic action into skin 42 at skin contact 42A in a manner described in the aforementioned commonly assigned U.S. patent applications.

Electrode 20 can be positioned as shown with or without reservoir 14 but in direct electrical contact with skin contact 42A. If reservoir 14 is used, a second drug may be placed in the reservoir different from the drug in reservoir 12. The drug in reservoir 14 would not be treated in the same manner as the drug in reservoir 12 and would migrate into skin or mucous membrane 42 at skin or mucous membrane contact 42A by electro-osmosis or by action of the ion repulsion relative to the polarity of battery 22A.

Reservoir 12 is optionally provided with a membrane 48 that separates reservoir 12 into a high concentration upper reservoir 12X and a low concentration lower reservoir 12Y. This type of reservoir separation is described in my prior U.S. patent application, Ser. No. 702,486.

Electrodes 16, 18 and 20 may alternately be an electrically conductive and permeable non-metallic membrane made of a depolarizing agent. Alternately, electrodes 16 and 18 may be metallic for conductive purposes but are coated with one of the depolarizing agents such as agent 50 known in the art such as manganese dioxide ($MnO_2$) that scrubs gas formations from the electrodes so as to cause any gas formed thereon to be chemically neutralized or absorbed in the gel. In addition, an outer layer of a semi-permeable membrane 52 may be added over agent 50 so as to keep the drug in reservoir 12B away from depolarizing agent 50.

FIG. 3 illustrates in schematic form the configuration described in FIGS. 1 and 2. FIG. 3 shows the migration of a drug A from reservoir 14 in particular from high concentration area 14X to low concentration area 14Y and from 14Y to and into skin or mucous membrane 42 of the patient. FIG. 3 also shows the movement of a drug B in the reservoir 12 from high concentration area 12X to low concentration area 12Y and then from area 12Y into skin or mucous membrane 42 of the patient. A control system 60 is shown in phantom lines positioned over electric components of system 10. Control system 60 includes a computer 62 positioned between a computer battery and computer output controls 66. An optional computer input, or programming input, 68 is positioned adjacent computer 62. Signal circuits are shown between computer output controls 66 and first and second batteries 22A and 24A shown as signal circuits 70, 72, 74 and 76 respectively. A signal circuit 78 extends between junction 26, which is adapted to be a switch, so that either path 28 and/or 30 is selected at the option of the user.

Signal circuits 70 and 72 are capable of reversing the polarity of batteries 22A and 24A respectively. Signal circuit 76 is capable of controlling the current passed between electrodes 16 and 18. An electrically activated switch 80 of the type known in the art is placed in electrical path 36. This switch 80 is normally in the off position when the system is not in use, for example, during shelf-life. When the system is activated by electrical contact between the electrode 18 and skin 42, switch 80 automatically closes. The entire system with control system 60 can be located in a housing 87 shown in phantom lines.

The invention described herein can also be assembled at the place of manufacture so as to construct the plurality of optional arrangements described above in individual units in accordance with the current requirements of the drug or drugs to be placed in the drug reservoirs for administration to the patient. The method of manufacture comprises the following steps:

(a) providing a first electrical circuit path through the skin having at least one reservoir containing two electrodes and a third electrode spaced from said reservoir;

(b) providing a second electrical circuit path in said reservoir interconnected to said first and second electrodes;

(c) providing at least one electrical power source positioned in either of said first or second electrical circuits; and (d) controlling the rate of delivery of said drug by establishing a selected current in accordance with any of the following options:

1. establishing only a first current in said first circuit path;

2. establishing only a second current in said second circuit path;

3. establishing an electrical path in said first circuit with said first electrode;

4. establishing a bypass electrical path in said first circuit with said second electrode bypassing said first electrode;

5. establishing the polarity of the said at least one power source; thus providing a predetermined rate of electrokinetic delivery for the drug.

The steps described above also include establishing a second power source in the other of the first or second electrical circuit paths. An additional step is establishing another drug reservoir about the third electrode.

The method of manufacture of the invention described herein may alternatively be described as comprising the following steps upon selection of a predetermined drug:

(a) providing a reservoir for containing the drug and placing spaced first and second electrodes in the reservoir, one side of the reservoir being provided with a permeable membrane, the first and second electrodes being spaced proximate to and distal respectively from the membrane, placing the particular drug in the reservoir and sealing the walls of the reservoir;

(b) providing a third electrode spaced from the reservoir;

(c) placing a path portion of a first electrical circuit extending from the third electrode with a junction spaced from the first electrode with a first power means and a first current conditioning means selected in accordance with the current desired in the reservoir as required by the drug, the polarity of the first power means being oriented with the current requirements;

(d) placing a second electrical circuit including a parallel circuit path with the first and second electrodes with a second power means and a second current conditioning means selected in accordance with the current desired in the reservoir as required by the drug, the polarity of the second means being oriented with the current requirements; and (e) placing either a first electrical path between the junction and the first electrode or a second electrical path between the junction and the second electrode in accordance with the current requirement of the drug.

Although the present invention has been described in some detail by way of illustration and example for purposes of clarity and understanding, it will, of course, be understood that various changes and modifications may be made in the form, details, and arrangements of the parts without departing from the scope of the invention as set forth in the following claims.

What is claimed is:

1. A system for selectively controlling the rate of delivery of a medicament or drug through the skin or mucous membrane of a human or animal by electrokinetic action, comprising, in combination:

drug reservoir means containing a drug, said drug reservoir means adapted to be in electrical contact with the skin at a first skin contact, said drug reservoir means retaining the drug and being capable of passing an electrical current through the drug wherein the drug is passed through the skin by electrokinetic action at said first skin contact, a pair of spaced first and second electrodes positioned in said drug reservoir means, said first and second electrodes being spaced apart from said first skin contact, electrode means in electrical contact with the skin at a second skin contact spaced from said skin contact, said electrode means being for passing and receiving current to and from said second skin contact, a first electrical circuit, formed when the system is mounted on the skin, extending between said first and second electrodes, between said second electrode and said electrode means through the skin wherein the skin acts as an electrical conductor, and said electrode means and said first electrode, said first electrical circuit including a bypass electrical circuit extending between a junction positioned on said first electrical circuit and said second electrode, said junction being positioned between said electrode means and said first electrode, wherein said bypass electrical circuit bypasses said first electrode.

a second electrical circuit extending in parallel between said first and second electrodes, first power means positioned in said first electrical circuit between said electrode means and said junction, said first power means being for generating a first electrical current through said first circuit, second power means positioned in said second electrical circuit adapted to pass a second electrical current through said second circuit, and means for passing a selected current between said first and second electrodes in accordance with the dosage and type of drug in said reservoir means, said means for passing a selected current including at least one of a plurality of the following options:

(a) selectively passing only said first current in said first circuit;

(b) selectively passing only said second current in said second circuit;

(c) selectively inactivating said bypass circuit;

(d) selectively using only said bypass circuit;

(e) selectively positioning the polarity of said first power means; and (f) selectively positioning the polarity of said first power means;

whereby a predetermined rate of electrokinetic delivery of said drug is attained.

2. A system in accordance with claim 1, further including a control system adapted to selectively operate said means for passing a selected current.

3. A system in accordance with claim 2, wherein said control system includes switch means positioned at said junction on said first circuit adapted to selectively activate or deactivate said bypass circuit and simultaneously to deactivate or activate, respectively, said first circuit between said junction and said first electrode.

4. A system according to claim 3, wherein said control system includes a computer system positioned proximate said first and second circuits, said computer system including signal circuits connected to said means for passing a selected current, computer originated output controls aligned with said signal circuits, and computer programming input circuitry capable of instructing said computer relative to operating said output controls.

5. A system according to claim 4, further including switch means positioned on said circuit path for deactivating said second electrical circuit, said switch means including switch means signal circuit connected to said output controls of said computer said computer programming input circuitry being capable of instructing said computer relative to said switch means signal circuit.

6. A system according to claim 3, wherein said reservoir means includes a semi-permeable membrane capable of passing the drug extending across said reservoir means generally between said first and second electrodes and forming first and second reservoirs, said first and second reservoirs being distal and proximate respectively to the skin of the patient, and said first drug being in generally concentrated form in said first reservoir and being in generally diluted form in said second reservoir.

7. A system in accordance with claim 6, said electrode means being another reservoir means containing a second drug, said electrode means including a third electrode positioned in said another reservoir means, said third electrode being in electrical contact with said first power means, said another reservoir means being capable of passing electrical current between said third electrode and said second skin contact.

8. A system according to claim 7, wherein said another reservoir means includes a semi-permeable membrane capable of passing said second drug extending across said reservoir forming third and fourth reservoirs, said third and fourth reservoirs being distal and proximate respectively to the skin of the patient, and said second drug being in generally concentrated form in said third reservoir and being in generally diluted form in said fourth reservoir.

9. A system according to claim 7, wherein said first, second and third electrodes are made of an electrically conductive and permeable non-metallic membrane containing a depolarizing agent.

10. A system according to claim 7, wherein said first, second and third electrodes are made of metal.

11. A system according to claim 10, further including coatings for said first, second and third electrodes, said coating being a depolarizing agent.

12. A system according to claim 11, wherein said depolarizing agent is manganese dioxide ($MnO_2$).

13. A system according to claim 12, further including outer layers over said coatings for said first, second and third electrodes, said outer layers being made of a semi-permeable membrane material capable of keeping said first and second drugs from contact with said depolarizing agent.

14. A system according to claim 1, further including first and second current conditioning means positioned in said first and second electrical circuits, respectively.

15. A system according to claim 14, wherein said first and second current conditioning means include a constant current device and a first timer in series and a second constant current device and a second timer in series.

16. A method of controlling the rate of electrokinetic delivery of a predetermined drug through the skin by means of a transdermal applicator comprising the following steps:
(a) providing a first electrical circuit path through the skin having at least one reservoir containing two electrodes and a third electrode spaced from said reservoir;
(b) providing a second electrical circuit path in said reservoir interconnected to said first and second electrodes;
(c) providing at least one electrical power source positioned in either of said first or second electrical circuits; and
(d) controlling the rate of delivery of said drug by establishing a selected current in accordance with any one of the following options:
 1. establishing only a first current in said first circuit path;
 2. establishing only a second current in said second circuit path;
 3. establishing an electrical path in said first circuit with said first electrode;
 4. establishing a bypass electrical path in said first circuit with said second electrode bypassing said first electrode;
 5. establishing the polarity of the said at least one power source; whereby a predetermined rate of electrokinetic delivery of said rug is attained.

17. The method according to claim 16, including a second power source in the other of said first or second electrical circuit paths.

18. The method according to claim 17, further including another drug reservoir positioned about said third electrode.

19. A method for manufacturing a drug applicator capable of selectively controlling the rate of delivery of a medicament or drug through the skin or mucous membrane of a human or animal patient by electrokinetic action, comprising the following steps:
(a) providing a reservoir for containing a predetermined drug and placing spaced first and second electrodes in said reservoir, one side of said reservoir being provided with a permeable membrane, said first and second electrodes being spaced proximate to and distal respectively from aid membrane, charging said drug in said reservoir;
(b) providing a third electrode spaced from said reservoir;
(c) providing a first electrical circuit path portion extending from said third electrode with a junction spaced from said first electrode with a first predetermined power means, the polarity of said first power means being oriented with drug current requirements;
(d) providing a second electrical circuit having a parallel circuit path with said first and second electrodes with second power means, the polarity of said second power means being oriented with drug current requirements; and
(e) providing either a first electrical path between said junction and said first electrode or a second electrical path between said junction and said second electrode in accordance with the current requirement of said predetermined drug.

20. The method according to claim 19, including sealing said reservoir.

21. The method according to claim 19, including providing first and second current conditioning means in said first and second electrical circuits respectively.

22. A method for manufacturing a drug applicator capable of selectively controlling the rate of delivery of a medicament or drug through the skin or mucous membrane of a human or animal patient by electrokinetic action, comprising the following steps:
 (a) providing a reservoir for containing a predetermined drug and placing spaced first and second electrodes in said reservoir, one side of said reservoir being provided with a permeable membrane, said first and second electrodes being spaced proximate to and distal respectively from said membrane, charging said drug in said reservoir;
 (b) providing a third electrode spaced from said reservoir;
 (c) providing a first electrical circuit path portion extending from said third electrode with a junction spaced from said first electrode with a first predetermined power means, the polarity of said first power means being oriented with drug current requirements;
 (d) providing a second electrical circuit having a parallel circuit path with said first and second electrodes with second electrodes with second power means, the polarity of said second power means being oriented with drug current requirements; and
 (e) providing switch means for selecting either a first electrical path between said junction and said first electrode or a second electrical path between said junction said second electrode in accordance with the current requirement of said predetermined drug.

* * * * *